(12) United States Patent
Wang

(10) Patent No.: US 7,501,255 B2
(45) Date of Patent: Mar. 10, 2009

(54) LEVELS OF PIN1 IN NORMAL AND CANCEROUS TISSUE

(75) Inventor: Da Gong Wang, Chestnut Hill, MA (US)

(73) Assignee: Pintex Pharmaceuticals, Inc., Watertown, MA (US)

( * ) Notice: Subject to any disclaimer, the term of this patent is extended or adjusted under 35 U.S.C. 154(b) by 544 days.

(21) Appl. No.: 10/713,392

(22) Filed: Nov. 14, 2003

(65) Prior Publication Data

US 2004/0171036 A1 Sep. 2, 2004

Related U.S. Application Data

(60) Provisional application No. 60/426,629, filed on Nov. 14, 2002.

(51) Int. Cl.
*G01N 33/53* (2006.01)
*G01N 33/574* (2006.01)

(52) U.S. Cl. ...................... 435/7.1; 435/7.23

(58) Field of Classification Search .............. 435/7.1; 530/350

See application file for complete search history.

(56) References Cited

U.S. PATENT DOCUMENTS

| 5,952,467 | A | * | 9/1999 | Hunter et al. ............... 530/350 |
| 5,972,697 | A | * | 10/1999 | Hunter et al. ............. 435/320.1 |
| 6,054,320 | A | * | 4/2000 | Patierno et al. .............. 436/64 |
| 6,057,116 | A | * | 5/2000 | Vielkind .................... 435/7.23 |
| 6,596,848 | B1 | | 7/2003 | Hunter et al. |
| 2002/0025521 | A1 | * | 2/2002 | Lu et al. ...................... 435/6 |
| 2003/0068626 | A1 | | 4/2003 | Wang et al. |

FOREIGN PATENT DOCUMENTS

WO WO-97/17986 A1 5/1997
WO WO-01/38878 A2 5/2001

OTHER PUBLICATIONS

Bao et al (American J of Pathology, 2004, 164:1727-1737).*
Kuramochi et al (J of Surgical Oncology, 2006, 94:155-160).*
Tockman et al (Cancer Res., 1992, 52:2711s-2718s).*
Greenbaum et al. (Genome Biology, 2003, vol. 4, Issue 9, pp. 117.1-117.8).*
He et al (Lung Cancer, 2007, 56:51-58).*
Steen et al (Trends in Biotechnology, 2002, 20:361-364).*
Tockman et al (Cancer Res., 1998, (Suppl), 52:2711s-2718).*
Dolinksi,Kara et al, "Peptidyl-prolyl isomerases—an overview of the cyclophilin, FKBP and parvulin families," *Guidebook to Molecular Chaperones and Protein-Folding Catalysts*, M.-J. eds. Gething, Oxford University Press, pp. 359-369.
Fujimori, Fumihiro et al, "Mice Lacking Pin1 Develop Normally, but Are Defective in Entering Cell Cycle from $G_0$ Arrest," *Biochemical and Biophysical Research Communications*, vol. 265:658-663 (1999).
Hunter, Tony, "Prolyl Isomerases and Nuclear Function," *Cell*, vol. 92:141-143 (1998).
Liou, Yih-Cherng et al, "Loss of Pin1 function in the mouse causes phenotypes resembling cyclin D1-null phenotypes," *PNAS*, vol. 99(3):1335-1340 (2002).
Lu, Kun Ping et al, "Pinning down proline-directed phosphorylation signaling," *TRENDS in Cell Biology*, vol. 12(4):164-172 (2002).
Lu, Kun Ping et al, "Evidence for a NIMA-like Mitotic Pathway in Vertebrate Cells," *Cell*, vol. 81:413-424 (1995).
Lu, Kun Ping et al, "A human peptidyl-prolyl isomerase essential for regulation of mitosis," *Nature*, vol. 380:544-547 (1996).
Lu, Kun Ping et al, "Properties and Regulation of the Cell Cycle-specific NIMA Protein Kinase of *Aspergillus nidulans*," *The Journal of Biological Chemistry*, vol. 268(12):8769-8776 (1993).
Lu, Pei-Jung et al, "The prolyl isomerase Pin1 restores the function of Alzheimer-associated phosphorylated tau protein," *Nature*, vol. 399:784-788 (1999).
Lu, Pei-Jung et al, "Function of WW Domains as Phosphoserine- or Phosphothreonine-Binding Modules," *Science*, vol. 283:1325-1328 (1999).
Ranganathan, Rama et al, "Structural and Functional Analysis of the Mitotic Romamase Pin1 Suggests Substrate Recognition Is Phosphorylation Dependent," *Cell*, vol. 89:875-886 (1997).
Rippmann, Joerg F. et al, "Phosphorylation-dependent Proline Isomerization Catalyzed by Pin1 Is Essential for Tumor Cell Survival and Entry into Mitosis," *Cell Growth & Differentiation*, vol. 11:409-416 (2000).
Shen, Minhui et al, "Characterization and cell cycle regulation of the related human telomeric proteins Pin2 and TRF1 suggest a role in mitosis," *Proc. Natl. Acad. Sci. USA*, vol. 94:13618-13623 (1997).
Shen, Minhui et al, "The essential mitotic peptidyl-prolyl isomerase Pin1 binds and regulates mitosis-specific phosphoproteins," *Genes & Dev.*, vol. 12:706-720 (1998).
Songyang, Zhou et al, "Catalytic specificity of protein-tyrosine kinases is critical for selective signalling," *Nature*, vol. 373-536-539 (1995).
Lu, Kun Ping et al, "The NIMA Kinase: A mitotic regulator in *Aspergillus nidulans* and vertebrate cells," *Progress in Cell Cycle Research*, vol. 1:187-205 (1995).
Uchida, Takafumi et al, "Identification and characterization of a 14 kDa human protein as a novel parvulin-like peptidyl prolyl *cis/trans* isomerase," *FEBS*, vol. 466:278-282 (1999).
Wulf, Gerburg et al, "Pin1 is overexpressed in breast cancer and cooperates with Ras signaling in increasing the transcriptional activity of c-Jun towards cyclin D1," *The EMBO Journal*, vol. 20(13):3459-3472 (2001).
Yaffe, Michael B. et al, "Sequence-Specific and Phosphorylation-Dependent Proline Isomerization: A Potential Mitotic Regulatory Mechanism," *Science*, vol. 278:1957-1960 (1997).
Zhou, X.Z. et al, "Phosphorylation-dependent prolyl isomerization: a novel signaling regulatory mechanism," *CMLS, Cell, Mol. Life. Sci.*, vol. 56:788-806 (1999).
Zhou, Xiao et al, "Pin1-Dependent Prolyl Isomerization Regulates Dephosphorylation of Cdc25C and Tau Proteins," *Molecular Cell*, vol. 6:873-883 (2000).

* cited by examiner

*Primary Examiner*—Laura B Goddard
(74) *Attorney, Agent, or Firm*—Lahive & Cockfield, LLP; Cynthia L. Kanik; Elizabeth A. Hanley, Esq.

(57) ABSTRACT

Methods for the use of Pin1 as a marker of abnormal cell growth are disclosed. In another embodiment, the method includes evaluating the efficacy of a treatment of an abnormal cell growth, such as cancer, by monitoring the levels of Pin1. The levels of Pin1 can be protein levels or nucleic acid levels.

14 Claims, 1 Drawing Sheet

SEQUENCE LISTING

<160> NUMBER OF SEQ ID NOS: 2

<210> SEQ ID NO 1
<211> LENGTH: 1014
<212> TYPE: DNA
<213> ORGANISM: Homo Sapiens

<400> SEQUENCE: 1

```
tgctggccag cacctcgagg gaag atg gcg gac gag gag aag ctg ccg ccc         51
                          Met Ala Asp Glu Glu Lys Leu Pro Pro
                           1               5 ggc tgg gag aag cgc atg agc cgc agc tca ggc cga gtg tac tac ttc         99
Gly Trp Glu Lys Arg Met Ser Arg Ser Ser Gly Arg Val Tyr Tyr Phe
 10              15                  20                  25 aac cac atc act aac gcc agc cag tgg gag cgc ccc agc ggc aac agc        147
Asn His Ile Thr Asn Ala Ser Gln Trp Glu Arg Pro Ser Gly Asn Ser
                 30                  35                  40 agc agt ggt ggc aaa aac ggg cag ggg gag cct gcc agg gtc cgc tgc        195
Ser Ser Gly Gly Lys Asn Gly Gln Gly Glu Pro Ala Arg Val Arg Cys
             45                  50                  55 tcg cac ctg ctg gtg aag cac agc cag tca cgg cgg ccc tcg tcc tgg        243
Ser His Leu Leu Val Lys His Ser Gln Ser Arg Arg Pro Ser Ser Trp
         60                  65                  70 cgg cag gag aag atc acc cgg acc aag gag gag gcc ctg gag ctg atc        291
Arg Gln Glu Lys Ile Thr Arg Thr Lys Glu Glu Ala Leu Glu Leu Ile
     75                  80                  85
```

```
aac ggc tac atc cag aag atc aag tcg gga gag gag gac ttt gag tct    339
Asn Gly Tyr Ile Gln Lys Ile Lys Ser Gly Glu Glu Asp Phe Glu Ser
 90              95                 100                 105 ctg gcc tca cag ttc agc gac tgc agc tca gcc aag gcc agg gga gac    387
Leu Ala Ser Gln Phe Ser Asp Cys Ser Ser Ala Lys Ala Arg Gly Asp
             110                 115                 120 ctg ggt gcc ttc agc aga ggt cag atg cag aag cca ttt gaa gac gcc    435
Leu Gly Ala Phe Ser Arg Gly Gln Met Gln Lys Pro Phe Glu Asp Ala
         125                 130                 135 tcg ttt gcg ctg cgg acg ggg gag atg agc ggg ccc gtg ttc acg gat    483
Ser Phe Ala Leu Arg Thr Gly Glu Met Ser Gly Pro Val Phe Thr Asp
     140                 145                 150 tcc ggc atc cac atc atc ctc cgc act gag tgagggtggg gagcccaggc      533
Ser Gly Ile His Ile Ile Leu Arg Thr Glu
 155                 160 ctggcctcgg ggcagggcag ggcggctagg ccggccagct ccccttgcc cgccagccag    593 tggccgaacc ccccactccc tgccaccgtc acacagtatt tattgttccc acaatggctg   653
ggagggggcc cttccagatt gggggccctg ggtccccac tccctgtcca tccccagttg    713
gggctgcgac cgccagattc tcccttaagg aattgacttc agcaggggtg ggaggctccc   773
agacccaggg cagtgtggtg ggagggggtgt tccaaagaga aggcctggtc agcagagccg   833
ccccgtgtcc cccaggtgc tggaggcaga ctcgagggcc gaattgtttc tagttaggcc    893
acgctcctct gttcagtcgc aaaggtgaac actcatgcgg cagccatggg ccctctgagc   953
aactgtgcag acctttcac ccccaattaa acccagaacc actaaaaaaa aaaaaaaaa   1013 a                                                                  1014

<210> SEQ ID NO 2
<211> LENGTH: 163
<212> TYPE: PRT
<213> ORGANISM: Homo Sapiens

<400> SEQUENCE: 2

Met Ala Asp Glu Glu Lys Leu Pro Pro Gly Trp Glu Lys Arg Met Ser
 1               5                  10                  15

Arg Ser Ser Gly Arg Val Tyr Tyr Phe Asn His Ile Thr Asn Ala Ser
             20                  25                  30

Gln Trp Glu Arg Pro Ser Gly Asn Ser Ser Ser Gly Lys Asn Gly
         35                  40                  45

Gln Gly Glu Pro Ala Arg Val Arg Cys Ser His Leu Leu Val Lys His
     50                  55                  60

Ser Gln Ser Arg Arg Pro Ser Ser Trp Arg Gln Glu Lys Ile Thr Arg
 65                  70                  75                  80

Thr Lys Glu Glu Ala Leu Glu Leu Ile Asn Gly Tyr Ile Gln Lys Ile
                 85                  90                  95

Lys Ser Gly Glu Glu Asp Phe Glu Ser Leu Ala Ser Gln Phe Ser Asp
             100                 105                 110

Cys Ser Ser Ala Lys Ala Arg Gly Asp Leu Gly Ala Phe Ser Arg Gly
         115                 120                 125

Gln Met Gln Lys Pro Phe Glu Asp Ala Ser Phe Ala Leu Arg Thr Gly
     130                 135                 140

Glu Met Ser Gly Pro Val Phe Thr Asp Ser Gly Ile His Ile Ile Leu
145                 150                 155                 160

Arg Thr Glu
```

LEVELS OF PIN1 IN NORMAL AND CANCEROUS TISSUE

RELATED APPLICATION

The current application claims priority from U.S. Provisional Application Ser. No. 60/426,629, entitled "Levels of Pin1 in Normal and Cancerous Tissue", which was filed on 14 Nov. 2002, which is incorporated by reference herein.

BACKGROUND OF THE INVENTION

The increased number of cancer cases reported in the United States, and, indeed, around the world, is a major concern. Currently there are only a handful of detection and treatment methods available for some specific types of cancer, and these provide no absolute guarantee of success. In order to be most effective, these treatments require not only an early detection of the malignancy, but a reliable assessment of the severity of the malignancy.

Cancers can be viewed as a breakdown in the communication between tumor cells and their environment, including their normal neighboring cells. Growth-stimulatory and growth-inhibitory signals are routinely exchanged between cells within a tissue. Normally, cells do not divide in the absence of stimulatory signals or in the presence of inhibitory signals. In a cancerous or neoplastic state, a cell acquires the ability to "override" these signals and to proliferate under conditions in which a normal cell would not.

In general, cancerous cells must acquire a number of distinct aberrant traits in order to proliferate in an abnormal manner. Reflecting this requirement is the fact that the genomes of certain well-studied tumors carry several different independently altered genes, including activated oncogenes and inactivated tumor suppressor genes. In addition to abnormal cell proliferation, cells must acquire several other traits for tumor progression to occur. For example, early on in tumor progression, cells must evade the host immune system. Further, as tumor mass increases, the tumor must acquire vasculature to supply nourishment and remove metabolic waste. Additionally, cells must acquire an ability to invade adjacent tissue. In many cases, cells ultimately acquire the capacity to metastasize to distant sites.

It is apparent that the complex process of tumor development and growth must involve multiple gene products. It is therefore important to define the role of specific genes involved in tumor development and growth, and to identify those genes and gene products that can serve as targets for the diagnosis, prevention and treatment of cancers.

Once it is known that a patient has cancer, it then becomes necessary to determine which method of treatment the patient will most benefit from. Part of this determination involves assessing which type of cancer the patient suffers from, which genes are involved in causing the cancer, and which tissue is specifically affected. There is a need in the art for methods to determine the appropriate treatment for subjects with cancer.

SUMMARY OF THE INVENTION

The invention relates to a method of detecting abnormal cell growth in a mammal, comprising the steps of detecting a level of Pin1 nucleic acid in a test sample; and comparing the level of Pin1 in the test sample with a level of Pin1 in a control sample wherein a lower level of Pin1 in the test sample as compared to the control sample is indicative of abnormal cell growth.

The invention relates to methods of treating a subject with abnormal cell growth, comprising assessing the level of Pin1 in a test sample from the mammal. The invention further relates to a method of deciding whether or not to treat a mammal with cancer with a Pin1 modulator. In one embodiment, the level of Pin-1 is a protein level. In another embodiment, the level of Pin1 is a nucleic acid level.

Specifically, in one embodiment the invention relates to test samples from skin, endometrium, adrenal gland, pancreas, intestine, stomach, kidney, or testis.

In particular, the invention relates to a method of treating abnormal cell growth in a mammal, comprising the steps of detecting a level of Pin1 in a test sample and comparing the level of Pin1 in the test sample with the level in a control sample. Decreased levels of Pin1 in a test sample as compared to a control level are indicitive that the subject has abnormal cell growth.

The invention further relates to a method of detecting abnormal cell growth in a mammal by assessing the level of Pin1 protein in a test sample from the mammal, comprising the steps of contacting the test sample with an antibody having specificity for Pin1 under conditions suitable for binding of the antibody to Pin1 thereby resulting in the formation of a complex between the antibody and Pin1; detecting the complex between the antibody and Pin1; and comparing the amount of the complex in the test sample with an amount of a complex in a control sample. The antibody can be a polyclonal or a monoclonal antibody and, optionally, detectably labeled. (e.g., radioactive, enzymatic, magnetic, biotinylated and/or fluorescence).

Another embodiment of the invention relates to a method of determining whether a subject would benefit from treatment of abnormal cell growth, comprising the steps of contacting a test sample obtained from the mammal with a nucleic acid probe to a Pin1 nucleic acid; maintaining the test sample and the nucleic acid probe under conditions suitable for a hybridization; detecting the hybridization between the test sample and the nucleic acid probe; and comparing the hybridization in the test sample from the mammal to a control test sample without abnormal cell growth, wherein an decrease in the hybridization signal in the test sample from the mammal compared to the control sample is indicative of abnormal cell growth that would be treatable with a Pin1 activator. The nucleic acid probe can be optionally labeled with a label comprising a fluorescent, radioactive, and enzymatic label.

In still another embodiment, the invention relates to a method of evaluating the efficacy of a treatment (e.g., surgery, radiation, chemotherapy) of abnormal cell growth in a mammal, comprising comparing a level of Pin1 in at least three test samples comprising a first test sample obtained at a first time, a second test sample obtained at a later second time, and a control sample obtained from normal tissue, wherein Pin1 levels approaching the level in the control sample indicates the efficacy of the treatment of the abnormal cell growth in the mammal.

In another embodiment, the invention relates to a kit for detecting an abnormal cell growth in a mammal comprising one or more reagents for detecting a level of Pin1 in a test sample obtained from the mammal. In particular, kits for Western blotting, imunocytochemistry, radioimmunoassays (RIA) and enzyme linked immunoabsorption assays are kits of the invention. Also included in the invention are kits, wherein the one or more reagents for detecting the abnormal cell growth are used for carrying out a nucleic acid amplification reaction, such as a polymerase chain reaction based assay.

Also included in the invention are kits for evaluating the efficacy of a cancer treatment in a mammal, comprising one or more reagents for detecting a level of Pin-1 in a test sample obtained from the mammal.

The invention also provides a method for facilitating the diagnosis of a state associated with abnormal cell growth in a subject, comprising detecting the level of a Pin1 marker in a sample from the subject as an indication of whether the subject has a state associated with abnormal cell growth, thereby facilitating the diagnosis of the subject. The invention further provides a method for facilitating the diagnosis of cancer in a subject, comprising detecting the level of a Pin1 marker in a sample from the subject as an indication of whether the subject has cancer, thereby facilitating the diagnosis of the subject. In related embodiments, the subject is receiving, or has received, therapy for a state associated with abnormal cell growth and the diagnosis is used to evaluate the subject's response to the therapy. In yet another related embodiment, the subject is involved in a therapy agent clinical trial and the diagnosis is used to evaluate the effectiveness of an agent of the clinical trial.

The invention described herein provides a packaged kit for carrying out a method of the invention, wherein the kit comprises at least one reagent for assaying levels of Pin1 in a sample from a subject, and instructions for using the at least one reagent to assay levels of Pin1 in a sample from a subject for the described method. The invention described herein further provides packaged kits for carrying out a method of the invention, wherein the kit comprises at least one Pin1 modulator, and instructions for using the Pin1 modulator in the described method.

The invention described herein also provides a pharmacogenomics method to determine which Pin1 activator a given patient or cancer type will respond to most favorably.

DETAILED DESCRIPTION OF THE INVENTION

Figure 1:
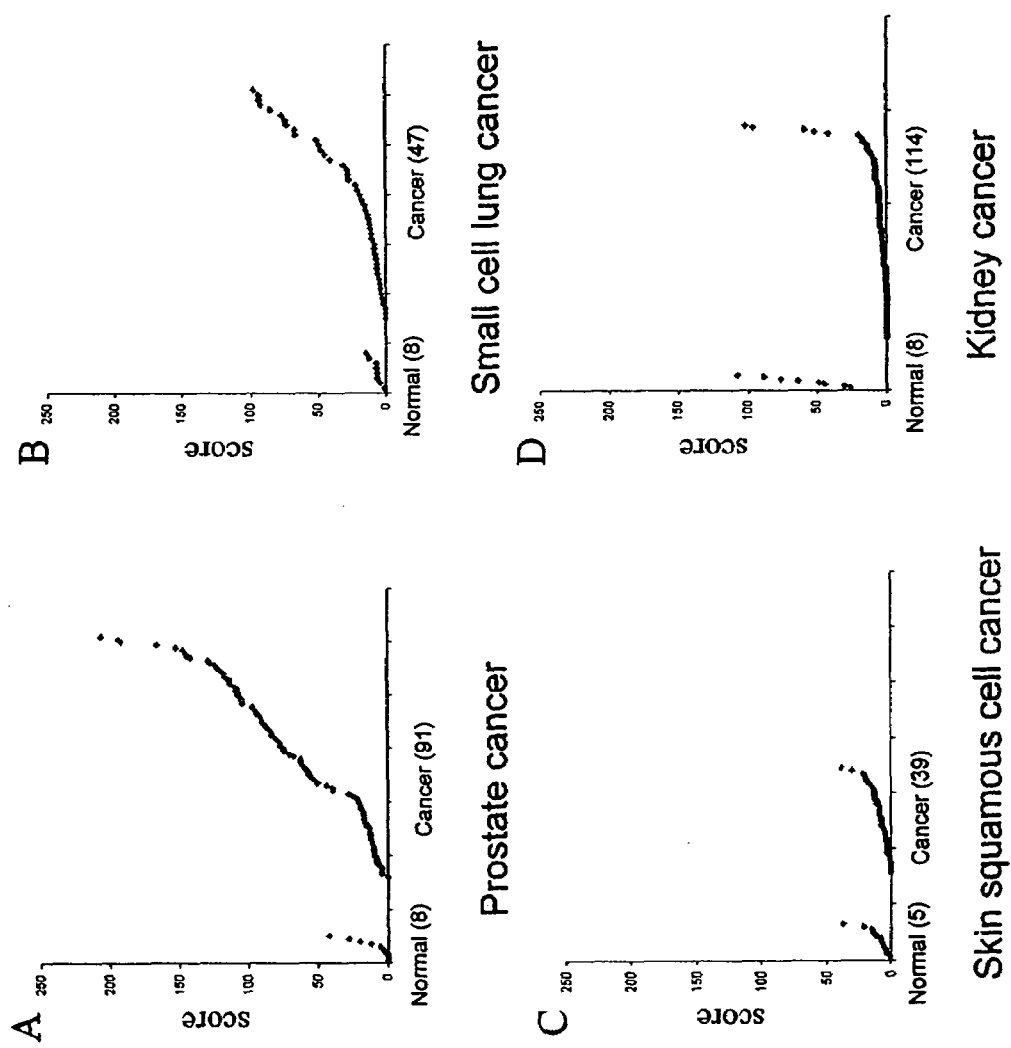
FIG. 1 is a graph that shows Pin1 levels in three representative categories of tumor tissues in comparison with corresponding normal tissues. Pin1 immunostaining was evaluated quantitatively using Automated Cellular Imaging System with the Pin1 Score=staining intensity+percentage of positive immunostaining. Overexpression of Pin1 in (A) prostate cancers and (B) small cell lung cancers. No change in Pin1 expression in (C) skin squamous cell cancers and underexpression of Pin1 in (D) kidney cancers.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to the discovery that the levels of Pin1 are decreased in certain cells undergoing abnormal cell growth. The present invention shows the levels of Pin1 in the normal tissues and cell types. The cell types are broken down into three categories. The first category contains normal human tissues that have low levels of Pin1 (Table 3). The second category contains normal human tissues that have moderate to high levels of Pin1 (Table 4). Lastly, the third category contains normal human tissues that have high levels of Pin1 (Table 5).

Comparison of the levels of Pin1 in cancerous human tissues to the levels of Pin1 in the corresponding normal tissues resulted in three distinct groups. The first group showed levels of Pin1 in cancerous tissue to be more than 10% higher than the levels of Pin1 in the corresponding normal tissues. In the second group, levels of Pin1 in the normal tissues and cancerous tissues were approximately equal. In the third group, levels of Pin1 in cancerous tissue was lower than levels of Pin1 in the corresponding normal tissue.

Uses and Methods of the Invention

The Pin1 markers (e.g., Pin1 nucleic acid molecules (SEQ ID NO: 1), Pin1 proteins (SEQ ID NO: 2), Pin1 protein homologues, and/or Pin1 antibodies) described in U.S. Pat. Nos. 5,972,697 and 5,952,467, and incorporated herein by reference, can be used in one or more methods which relate to Pin1-associated disorders, including: a) screening assays; b) predictive medicine (e.g., diagnostic assays, prognostic assays, monitoring clinical trials, and "Subject" includes living organisms, e.g., prokaryotes and eukaryotes. Examples of subjects include mammals, e.g., humans, dogs, cows, horses, kangaroos, pigs, sheep, goats, cats, mice, rabbits, rats, and transgenic non-human animals. Most preferably the subject is a human.

As used herein, the term "Pin1-associated disorder" includes a disorder or a state (e.g., a disease state) which is associated with abnormal cell growth, abnormal cell proliferation, or aberrant levels of Pin1 marker. Pin1-associated disorders include cancers, malignancies, tumors, and proliferative arthritic conditions. Pin1-associated disorders further include disorders which are not specific to a given tissue or cell type (e.g., a Pin1-associated disorder may present in a variety of tissues or cell types).

As used herein, the term "abnormal cell growth" is intended to include cell growth which is undesirable or inappropriate. Abnormal cell growth also includes proliferation which is undesirable or inappropriate (e.g., unregulated cell proliferation or undesirably rapid cell proliferation). Abnormal cell growth can be benign and result in benign masses of tissue or cells, or benign tumors. Many art-recognized conditions are associated with such benign masses or benign tumors including diabetic retinopathy, retrolental fibroplasia, neovascular glaucoma, psoriasis, angiofibromas, rheumatoid arthritis, hemangiomas, and Karposi's sarcoma. Abnormal cell growth can also be malignant and result in malignancies, malignant masses of tissue or cells, or malignant tumors. Many art-recognized conditions and disorders are associated with malignancies, malignant masses, and malignant tumors including cancer and carcinoma.

As used herein, the term "tumor" is intended to encompass both in vitro and in vivo tumors that form in any organ of the body. Tumors may be associated with benign abnormal cell growth (e.g., benign tumors) or malignant cell growth (e.g., malignant tumors).

"Cancer" includes a malignant neoplasm characterized by deregulated or uncontrolled cell growth. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The histological features of cancer are summarized by the term "anaplasia." Malignant neoplasms often contain numerous mitotic cells. These cells are typically abnormal. Such mitotic aberrations account for some of the karyotypic abnormalities found in most cancers. Bizarre multinucleated cells are also seen in some cancers, especially those which are highly anaplastic. "Dyplasia" refers to a pre-malignant state in which a tissue demonstrates histologic and cytologic features intermediate between normal and anaplastic. Dysplasia is often reversible.

"Anaplasia" refers to the histological features of cancer. These features include derangement of the normal tissue architecture, the crowding of cells, lack of cellular orientation termed dyspolarity, cellular heterogeneity in size and shape termed "pleomorphism." The cytologic features of anaplasia include an increased nuclear-cytoplasmic ratio (the nuclear-cytoplasmic ratio can be over 50% for maligant cells), nuclear pleomorphism, clumping of the nuclear chromatin along the nuclear membrane, increased staining of the nuclear chromatin, simplified endoplasmic reticulum, increased free ribosomes, pleomorphism of mitochondria, decrease in size and number of organelles, enlarged and increased numbers of nucleoli, and sometimes the presence of intermediate filaments.

"Neoplasia" or "neoplastic transformation" is the pathologic process that results in the formation and growth of a neoplasm, tissue mass, or tumor. Such process includes uncontrolled cell growth, including either benign or malignant tumors. Neoplasms include abnormal masses of tissue, the growth of which exceeds and is uncoordinated with that of the normal tissues and persists in the same excessive manner after cessation of the stimuli which evoked the change. Neoplasms may show a partial or complete lack of structural organization and functional coordination with the normal tissue, and usually form a distinct mass of tissue.

Neoplasms tend to morphologically and functionally resemble the tissue from which they originated. For example, neoplasms arising within the islet tissue of the pancreas resemble the islet tissue, contain secretory granules, and secrete insulin. Clinical features of a neoplasm may result from the function of the tissue from which it originated.

By assessing the histologic and other features of a neoplasm, it can be determined whether the neoplasm is benign or malignant. Invasion and metastasis (the spread of the neoplasm to distant sites) are definitive attributes of malignancy. Despite the fact that benign neoplasms may attain enormous size, they remain discrete and distinct from the adjacent non-neoplastic tissue. Benign tumors are generally well circumscribed and round, have a capsule, and have a grey or white color, and a uniform texture. By contrast, malignant tumor generally have fingerlike projections, irregular margins, are not circumscribed, and have a variable color and texture. Benign tumors grow by pushing on adjacent tissue as they grow. As the benign tumor enlarges it compresses adjacent tissue, sometimes causing atrophy. The junction between a benign tumor and surrounding tissue may be converted to a fibrous connective tissue capsule allowing for easy surgical remove of benign tumors. By contrast, malignant tumors are locally invasive and grow into the adjacent tissues usually giving rise to irregular margins that are not encapsulated making it necessary to remove a wide margin of normal tissue for the surgical removal of malignant tumors. Benign neoplasms tends to grow more slowly than malignant tumors. Benign neoplasms also tend to be less autonomous than malignant tumors. Benign neoplasms tend to closely histologically resemble the tissue from which they originated. More high differentiated cancers, cancers that resemble the tissue from which they originated, tend to have a better prognosis than poorly differentiated cancers. Malignant tumors are more likely than benign tumors to have an aberrant function (i.e. the secretion of abnormal or excessive quantities of hormones).

As used herein, the term "Pin1 marker" refers to a marker which is capable of being indicative of Pin1 levels in a sample of the invention. Pin1 markers include nucleic acid molecules (e.g., mRNA, DNA) which corresponds to some or all of a Pin1 gene, peptide sequences (e.g., amino acid sequences) which correspond to some or all of a Pin1 protein, peptide sequences which are homologous to Pin1 peptide sequences, antibodies to Pin1 protein, substrates of Pin1 protein, binding partners of Pin1 protein, and activity of Pin1.

The isolated nucleic acid molecules of Pin1 can be used, for example, to detect Pin1 mRNA (e.g., Pin1 nucleic acid marker in a biological sample) or a genetic alteration in a Pin1 gene. Moreover, the anti-Pin1 antibodies of the invention can be used to detect levels of Pin1 in a biological sample.

A. Screening Assays for Modulators and/or Inhibitors:

One major goal in cancer treatment has been to prevent the unregulated cell proliferation and, even better, to specifically kill dividing cancer cells. Interestingly, mitotic checkpoint controls have been identified as key targets for anticancer therapeutic procedures for two major reasons. First, since mitosis is a tightly regulated and orderly process, anticancer drugs that target at mitotic checkpoint controls can kill cells, often by inducing mitotic arrest followed by apoptosis. This is in contrast to those anticancer drugs that target other phase of the cell cycle, which just stop cells from continuous growing, but do not kill them. One of the best examples is the microtubule modifying agents, such as Oncovin and Taxols, which have been proven to be powerful drugs in treating various tumors (Piccart and Di Leo (1997) *Semin Oncol* 24:S10-27-S10-33). Second, abrogation of G2/M checkpoint have been shown to improve radiation therapy (Meyn (1997) *Oncology* 11:349-56 (see also discussion on pages 356, 361 and 365); Muschel et al. (1997) *Vitam Horm* 53:1-25). Since effective radiation therapy has been shown to induces cell cycle arrest in G2 and M, and subsequent apoptosis, drugs that disrupt mitotic checkpoints would have a cooperative effect with irradiation in killing cancer cells. For at least the following reasons, Pin1 is be a potential novel drug target.

Pin1 is underexpressed in a variety of human cancer samples, including, but not limited to those disclosed in Table 1.

B. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for measuring levels of Pin1 marker in the context of a biological sample to thereby determine whether an individual is afflicted with a disease or disorder, or is at risk of developing a disorder, associated with aberrant Pin1 expression or activity (e.g., abnormal or indignant cell growth, tumors, cancer). The invention also provides for prognostic (or predictive) assays for determining whether an individual is at risk of developing a disorder associated with a Pin1 marker. The invention further provides for prognostic (or predictive) assays for determining the stage of a Pin1-associated disorder.

As used herein, the term "stage" includes the degree of progression of a disease. Examples of Pin1-associated disorders which may have stages assigned to them include cancers, malignancies, abnormal cell growth, and tumors. Considerations for assigning stages to such disorders include level of metastases (if metastatic at all) of a cancer or malignancy, and level of aggressiveness of a cancer or malignancy. Other generally accepted criteria for assigning stages to such disorders are well known to one skilled in the art.

Another aspect of the invention pertains to monitoring the effectiveness of agents (e.g., drugs, compounds, anti-cancer agents) on the expression or activity of Pin1 in clinical trials.

These and other agents are described in further detail in the following sections.

1. Diagnostic Assays

An exemplary method for detecting the level of Pin1 protein or nucleic acid in a biological sample involves obtaining a biological sample from a test subject and contacting the biological sample with a compound or an agent capable of detecting Pin1 protein or nucleic acid (e.g., mRNA, genomic DNA) that encodes Pin1 protein such that the presence of Pin1 protein or nucleic acid is detected in the biological sample. A preferred agent for detecting Pin1 mRNA or genomic DNA is a labeled nucleic acid probe capable of hybridizing to Pin1 mRNA or DNA. The nucleic acid probe can be, for example, a Pin1 nucleic acid or a corresponding nucleic acid such as an oligonucleotide of at least 15, 30, 50, 100, 250 or 500 nucleotides in length which is capable of specifically hybridizing under stringent conditions to Pin1 mRNA or genomic DNA. Other suitable probes for use in the diagnostic assays of the invention are described herein.

In addition, this invention provides a method for diagnosing cancer in a subject, comprising: (a) obtaining a tissue sample from the subject; (b) contacting the tissue sample with an attached antibody to Pin1 to form a Pin1-antibody complex, wherein the attached antibody is attached to a solid phase; (c) contacting the Pin1-antibody complex with a probe antibody, wherein the probe antibody binds to a second site on Pin1; and (d) determining the amount of binding of the probe antibody to the tissue sample.

This invention provides a method for measuring the aggressiveness of cancer in a subject, comprising: (a) obtaining a cancer tissue sample from the subject; (b) contacting the tissue sample with an antibody to Pin1 or a fragment thereof to form a complex between the antibody and Pin1; (c) determining the amount of binding of the antibody to the tissue sample; and (d) comparing the amount of antibody bound to the tissue sample to a predetermined base level to measure the aggressiveness of the cancer, wherein increased amounts of the antibody bound to the tissue sample are diagnostic of a more aggressive cancer.

This invention further provides a method for identifying cancer likely to metastasize in a subject, comprising: (a) obtaining a cancer tissue sample from the subject; (b) contacting the tissue sample with an antibody to Pin1 to form a complex between the antibody and Pin1; (c) determining the amount of binding of the antibody to the tissue sample; and (d) comparing the amount of antibody bound to the tissue sample to a predetermined base level to measure the likelihood of the cancer to metastasize, wherein increased amounts of the antibody bound to the tissue sample are diagnostic of a cancer likely to metastasize.

In the above methods, the amount of the complex between the antibody and Pin1 is determined by the intensity of the signal emitted by the labeled antibody or by the number cells in the tissue sample bound to the labeled antibody.

The above diagnostic and prognostic methods may be used in combination with other above diagnostic and prognostic methods. For example, the above methods may used on a subject or mammal that was identified by a blood test as possibly having cancer.

Antibodies

"Antibody" includes immunoglobulin molecules and immunologically active determinants of immunoglobulin molecules, i.e., molecules that contain an antigen binding site which specifically binds (immunoreacts with) an antigen. Antibody includes polyclonal antibodies, monoclonal antibodies, whole immunoglobulins, and antigen binding fragments of the immunoglobulins. Antibodies specific for Pin1 can be specific for phosphorylated Pin1, unphosphorylated Pin1, or specific Pin1 independent of phosphorylation state. Exemplary Pin1 antibodies are described in U.S. Pat. No. 6,596,848, the contents of which is incorporated herein by reference.

Antibody fragments are obtained using conventional techniques well-known to those with skill in the art, and the fragments are screened for utility in the same manner as are intact antibodies. The term "antibody" is further intended to include bispecific and chimeric molecules having at least one antigen binding determinant derived from an antibody molecule.

In the diagnostic and prognostic assays of the invention, the antibody can be a polyclonal antibody or a monoclonal antibody and in a preferred embodiment is a labeled antibody.

Polyclonal antibodies are produced by immunizing animals, usually a mammal, by multiple subcutaneous or intraperitoneal injections of an immunogen (antigen) and an adjuvant as appropriate. As an illustrative embodiment, animals are typically immunized against a protein, peptide or derivative by combining about 1 µg to 1 mg of protein capable of eliciting an immune response, along with an enhancing carrier preparation, such as Freund's complete adjuvant, or an aggregating agent such as alum, and injecting the composition intradermally at multiple sites. Animals are later boosted with at least one subsequent administration of a lower amount, as ⅕ to ⅒ the original amount of immunogen in Freund's complete adjuvant (or other suitable adjuvant) by subcutaneous injection at multiple sites. Animals are subsequently bled, serum assayed to determine the specific antibody titer, and the animals are again boosted and assayed until the titer of antibody no longer increases (i.e., plateaus).

"Monoclonal antibody" or "monoclonal antibody composition" as used herein refers to a preparation of antibody molecules of single molecular composition. A monoclonal antibody composition displays a single binding specificity and affinity for a particular epitope. Monoclonal antibodies can be prepared using a technique which provides for the production of antibody molecules by continuous growth of cells in culture. These include but are not limited to the hybridoma technique originally described by Kohler and Milstein (1975, *Nature* 256:495-497; see also Brown et al. 1981 *J. Immunol* 127:539-46; Brown et al., 1980, *J Biol Chem* 255:4980-83; Yeh et al., 1976, PNAS 76:2927-31; and Yeh et al., 1982, *Int. J. Cancer* 29:269-75) and the more recent human B cell hybridoma technique (Kozbor et al., 1983, *Immunol Today* 4:72), EBV-hybridoma technique (Cole et al., 1985, Monoclonal Antibodies and Cancer Therapy, Alan R. Liss, Inc., pp. 77-96), and trioma techniques.

The fusion-product cells, which include the desired hybridomas, are cultured in selective medium such as HAT medium, designed to eliminate unfused parental myeloma or lymphocyte or spleen cells. Hybridoma cells are selected and are grown under limiting dilution conditions to obtain isolated clones. The supernatants of each clonal hybridoma is screened for production of antibody of desired specificity and affinity, e.g., by immunoassay techniques to determine the desired antigen such as that used for immunization. Monoclonal antibody is isolated from cultures of producing cells by conventional methods, such as ammonium sulfate precipitation, ion exchange chromatography, and affinity chromatography (Zola et al., Monoclonal Hybridoma Antibodies: Techniques And Applications, Hurell (ed.), pp. 51-52, CRC Press, 1982). Hybridomas produced according to these methods can be propagated in culture in vitro or in vivo (in ascites fluid) using techniques well known to those with skill in the art.

"Labeled antibody" as used herein includes antibodies that are labeled by a detectable means and includes enzymatically, radioactively, fluorescently, chemiluminescently, and/or bioluminescently labeled antibodies.

One of the ways in which an antibody can be detectably labeled is by linking the same to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the Pin1-specific antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection may be accomplished using any of a variety of immunoassays. For example, by radioactively labeling an antibody, it is possible to detect the antibody through the use of radioimmune assays. A description of a radioimmune assay (RIA) may be found in Laboratory Techniques and Biochemistry in Molecular Biology, by Work, T. S., et al., North Holland Publishing Company, N.Y. (1978), with particular reference to the chapter entitled "An Introduction to Radioimmune Assay and Related Techniques" by Chard, T.

The radioactive isotope can be detected by such means as the use of a gamma counter or a scintillation counter or by audioradiography. Isotopes which are particularly useful for the purpose of the present invention are: $^3H$, $^{131}I$, $^{35}S$, $^{14}C$, and preferably $^{125}I$.

It is also possible to label an antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}Eu$, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

Likewise, a bioluminescent compound may be used to label an antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Additionally, antibodies directed toward a protein of interest can be connected to magnetic beads and used to enrich a population. Immunomagnetic selection has been used previously for this purpose and examples of this method can be found, for example, at U.S. Pat. No. 5,646,001; Ree et al. (2002) *Int. J. Cancer* 97:28-33; Molnar et al. (2001) *Clin. Cancer Research* 7:4080-4085; and Kasimir-Bauer et al. (2001) *Breast Cancer Res. Treat.* 69:123-32. An antibody, either polyclonal or monoclonal, that is specific for a cell surface protein on a cell of interest can be attacthed to a magnetic substrate thereby allowing selection of only those cells that express the surface protein of interest. The selected cells can then be lysed and the cellular contents assayed for the presence of Pin1.

In the diagnostic and prognostic assays of the invention, the amount of binding of the antibody to the tissue sample can be determined by the intensity of the signal emitted by the labeled antibody and/or by the number cells in the tissue sample bound to the labeled antibody.

Immunoassays

The amount of an antigen (i.e. Pin1) in a tissue sample may be determined by a radioimmunoassay, an immunoradiometric assay, and/or an enzyme immunoassay. Further, the amount of a specific type of antigen (e.g., phosphorylated or unphosphorylated) in a tissue sample may be determined using for example a phosphorylation specific antibody to Pin1 in a radioimmunoassay, an immunoradiometric assay, and/or an enzyme immunoassay.

"Radioimmunoassay" is a technique for detecting and measuring the concentration of an antigen using a labeled (i.e. radioactively labeled) form of the antigen. Examples of radioactive labels for antigens include $^3H$, $^{14}C$, and $^{125}I$. The concentration of antigen (i.e. Pin1) in a sample (i.e. tissue sample) is measured by having the antigen in the sample compete with a labeled (i.e. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (i.e. covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the test sample can be determined.

A "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." The "Enzyme-Linked Immunosorbent Assay (ELISA)" is a technique for detecting and measuring the concentration of an antigen using a labeled (i.e. enzyme linked) form of the antibody.

In a "sandwich ELISA", an antibody (i.e. to Pin1) is linked to a solid phase (i.e. a microtiter plate) and exposed to a test sample containing antigen (i.e. Pin1). The solid phase is then washed to remove unbound antigen. A labeled (i.e. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and β-galactosidase. The enzyme linked antibody reacts with a substrate to generate a colored reaction product that can be assayed for.

In a "competitive ELISA", antibody is incubated with a sample containing antigen (i.e. Pin1). The antigen-antibody mixture is then contacted with an antigen-coated solid phase (i.e. a microtiter plate). The more antigen present in the sample, the less free antibody that will be available to bind to the solid phase. A labeled (i.e. enzyme linked) secondary antibody is then added to the solid phase to determine the amount of primary antibody bound to the solid phase.

A preferred agent for detecting Pin1 marker is an antibody capable of binding to Pin1 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

With respect to antibody-based detection techniques, one of skill in the art can raise anti-Pin1 antibodies against an appropriate immunogen, such as isolated and/or recombinant Pin1 or a portion or fragment thereof (including synthetic molecules, such as synthetic peptides) using no more than routine experimentation. Synthetic peptides can be designed and used to immunize animals, such as rabbits and mice, for antibody production. The nucleic and amino acid sequence of Pin1 is known (Hunter et al., WO 97/17986 (1997); Hunter et al., U.S. Pat. Nos. 5,952,467 and 5,972,697, the teachings of all of which are hereby incorporated by reference in their entirety) and can be used to design nucleic acid constructs for producing proteins for immunization or in nucleic acid detection methods or for the synthesis of peptides for immunization. Conditions for incubating an antibody with a test sample can vary depending upon the tissue or cellular type. Incubation conditions can depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques," Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of enzyme Immunoassays: Laboratory Techniques in Biochemistry and Molecular Biology," Elsevier Science Publishers, Amsterdam, The Netherlands (1985).

As used herein, the terms "sample," "test sample," "tissue sample," and "biological sample" include samples obtained from a mammal or a subject containing Pin1 which can be used within the methods described herein, e.g., tissues, cells and biological fluids isolated from a subject, as well as tissues, cells and fluids present within a subject. "Tissue samples" include solid and liquid tissue samples. Examples of solid tissue samples tissues from the kidney, testis, skin, adrenal gland, and stomach. Examples of "liquid tissue samples" or "body fluid samples" include samples taken from the blood, serum, semen, prostate fluid, seminal fluid, urine, saliva, sputum, phlegm, pus, mucus, bone marrow, lymph, ascites and tears. For amplifying Pin1 RNA, the preferred tissue sample is a peripheral venous blood sample.

Accordingly, the detection method of the invention can be used to detect Pin1 mRNA, protein, or genomic DNA in a biological sample in vitro as well as in vivo. For example, in vitro techniques for detection of Pin1 mRNA include Northern hybridizations and in situ hybridizations. In vitro techniques for detection of Pin1 protein include enzyme linked immunosorbent assays (ELISAs), Western blots, immunoprecipitations and immunofluorescence. In vitro techniques for detection of Pin1 genomic DNA include Southern hybridizations. Furthermore, in vivo techniques for detection of Pin1 protein include introducing into a subject a labeled anti-Pin1 antibody. For example, the antibody can be labeled with a radioactive marker whose presence and location in a subject can be detected by standard imaging techniques.

In another embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Pin1 marker such that the presence of Pin1 marker is detected in the biological sample, and comparing the presence of Pin1 marker in the control sample with the presence of Pin1 marker in the test sample.

The immunological assay test samples of the present invention may include cells, protein or membrane extracts of cells, blood or biological fluids. The test sample used in the above-described method is based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized. The invention also encompasses kits for detecting the presence of Pin1 in a biological sample. For example, the kit can comprise a labeled compound or agent capable of detecting Pin1 protein or mRNA in a biological sample; means for determining the amount of Pin1 in the sample; and means for comparing the amount of Pin1 in the sample with a standard. The compound or agent can be packaged in a suitable container. The kit can further comprise instructions for using the kit to detect Pin1 protein or nucleic acid.

A compartmentalized kit can include any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe, primers or antibodies used in the assay, containers which contain wash reagents (such as phosphate buffered saline, Tris-buffers, and the like), and containers which contain the reagents used to detect the hybridized probe, bound antibody, amplified product, or the like.

The kits are used to detect and distinguish normal cells from cells undergoing abnormal cell growth. Additionally, or alternatively, the kits are used to distinguish between aggressive or various stages of an abnormal cell growth or to distinguish between benign or malignant forms of abnormal cell growth in tumors. It is also envisioned that the kits and methods of the invention can be used to define the need for treatment of abnormal cell growths, such as surgical interventions, types of chemotherapeutic drugs or radiation treatments.

The kits and methods of the invention are used to detect metastasis of abnormally cell growths. A "metastasis" is the spread of an abnormal cell growth from one part of the body (e.g., breast tissue, prostate gland, uterus, skin, testes, ovary) to another part of the body (e.g., breast, prostate, uterus, brain, skin, testes, ovary, lymph nodes). The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler, et al., Adv. Cancer Res. 28, 149-250 (1978), Liotta, et al., Cancer Treatment Res. 40, 223-238 (1988), Nicolson, Biochim. Biophy. Acta 948, 175-224 (1988) and Zetter, N. Eng. J. Med. 322, 605-612 (1990)). Increased malignant cell motility has been associated with enhanced metastatic potential in animal as well as human tumors (Hosaka, et al., Gann 69, 273-276 (1978) and Haemmerlin, et al., Int. J. Cancer 27, 603-610 (1981)).

One skilled in the art will readily recognize that the nucleic acid probes described in the present invention can readily be incorporated into one of the established kit formats which are well known in the art.

In the embodiments of the invention described herein, well known biomolecular methods such as northern blot analysis, RNase protection assays, southern blot analysis, western blot analysis, in situ hybridization, immunocytohemical procedures of tissue sections or cellular spreads, and nucleic acid amplification reactions (e.g., polymerase chain reactions) may be used interchangeably. One of skill in the art would be capable of performing these well-established protocols for the methods of the invention. (See, for example, Ausubel, et al., "Current Protocols in Moleculer Biology," John Wiley & Sons, New York, N.Y. (1999)).

2. Prognostic Assays

The diagnostic methods described herein can furthermore be utilized to identify subjects having or at risk of developing a disease or disorder associated with aberrant Pin1 expression or activity. For example, the assays described herein, such as the preceding diagnostic assays or the following assays, can be utilized to identify a subject having or at risk of developing a disorder associated with Pin1 marker (e.g., abnormal or malignant cell growth, tumors, cancer). Thus, the present invention provides a method for identifying a disease or disorder associated with aberrant Pin1 expression or activity in which a test sample is obtained from a subject and Pin1 protein or nucleic acid (e.g., mRNA, genomic DNA) is detected, wherein the decreased level of Pin1 protein or nucleic acid is diagnostic for a subject having or at risk of developing a Pin1-associated disorder.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Pin1 expression or activity. Thus, the present invention provides methods for determining whether a subject can be effectively treated with an agent for a disorder associated with aberrant Pin1 expression or activity in which a test sample is obtained and Pin1 protein or nucleic acid expression or activity is detected.

In certain embodiments, a biological sample can be evaluated using the methods disclosed herein to determine the amount of Pin1 in the nucleus of the cells. Conversely, the sample can be evaluated for the amount of Pin1 in the cytoplasm of the cells In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the Pin1-gene (see Abravaya et al. (1995) *Nucleic Acids Res.* 23:675-682). This method can include the steps of collecting a sample from a patient, isolating nucleic acid (e.g., genomic, mRNA or both) from the sample, contacting the nucleic acid sample with one or more primers which specifically hybridize to a Pin1 gene under conditions such that hybridization and amplification of the Pin1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al., (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

Any cell type or tissue in which Pin1 is expressed may be utilized in the prognostic assays described herein.

3. Monitoring of Effects During Clinical Trials

Monitoring the influence of agents (e.g., drugs or compounds) on the expression or activity of a Pin1 protein can be applied not only in basic drug screening, but also in clinical trials. For example, the effectiveness of an agent determined by a screening assay as described herein to increase Pin1 gene expression, protein levels, or upregulate Pin1 activity, can be monitored in clinical trials of subjects exhibiting decreased Pin1 gene expression, protein levels, or downregulated Pin1 activity. In such clinical trials, the expression or activity of a Pin1 gene, and preferably, other genes that have been implicated in a disorder can be used as a "read out" or markers of the phenotype of a particular cell.

For example, and not by way of limitation, genes, including Pin1, that are modulated in cells by treatment with an agent (e.g., compound, drug or small molecule) which modulates Pin1 activity (e.g., identified in a screening assay as described herein) can be identified. Thus, to study the effect of agents on a Pin1 associated disorder, for example, in a clinical trial, cells can be isolated and RNA prepared and analyzed for the levels of expression of Pin1 and other genes implicated in the Pin1 associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of Pin1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a Pin1 protein, mRNA, or genomic DNA in the pre-administration sample; (iii) obtaining one or more post-administration samples from the subject; (iv) detecting the level of expression or activity of the Pin1 protein, mRNA, or genomic DNA in the post-administration samples; (v) comparing the level of expression or activity of the Pin1 protein, mRNA, or genomic DNA in the pre-administration sample with the Pin1 protein, mRNA, or genomic DNA in the post administration sample or samples; and (vi) determining if the Pin1 level is approaching the Pin1 level in a control sample and altering the administration of the agent to the subject accordingly.

C. Methods of Treatment:

The present invention provides for both prophylactic and therapeutic methods of treating a subject at risk of (or susceptible to) a disorder or having a disorder associated with aberrant Pin1 expression or activity (e.g., abnormal or malignant cell growth, tumors, cancer).

In another embodiment of the above methods of treating abnormal cell growth or cancer, the abnormal cell growth or tumor growth or cancer is caused by overexpression of Pin1. In a preferred embodiment, the abnormal cell growth or tumor growth or cancer being treated is breast cancer, prostate cancer, or leukemia.

"Treatment", as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the Pin1 molecules of the present invention or Pin1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant Pin1 expression or activity, by administering to the subject a Pin1 or an agent which modulates Pin1 expression or at least one Pin1 activity. Subjects at risk for a disease which is caused or contributed to by aberrant Pin1 expression or activity can be identified by, for example, any of a combination of diagnostic or prognostic assays as described herein. Administration of a prophylactic agent can occur prior to the manifestation of symptoms characteristic of the Pin1 aberrancy, such that a disease or disorder is prevented or, alternatively, delayed in its progression. Depending on the type of Pin1 aberrancy, for example, a Pin1 agonist agent can be used for treating the subject. The appropriate agent can be determined based on screening assays described herein.

2. Therapeutic Methods

Another aspect of the invention pertains to methods of modulating Pin1 expression or activity for therapeutic purposes. Accordingly, in an exemplary embodiment, the modulatory method of the invention involves contacting a cell with a Pin1 or agent that modulates one or more of the activities of Pin1 protein activity associated with the cell. An agent that modulates Pin1 protein activity can be an agent as described herein, such as a nucleic acid or a protein, a naturally-occurring target molecule of a Pin1 protein (e.g., a phosphoprotein), a Pin1 antibody, a Pin1 agonist or antagonist, a peptidomimetic of a Pin1 agonist or antagonist, or other small molecule. In one embodiment, the agent stimulates one or more Pin1 activities. Examples of such stimulatory agents include active Pin1 protein and a nucleic acid molecule encoding Pin1 that has been introduced into the cell. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by decreased expression or activity of a Pin1 protein or nucleic acid molecule. In one embodiment, the method involves administering an agent (e.g., an agent identified by a screening assay described herein), or combination of agents that modulates (e.g., upregulates) Pin1 expression or activity. In another embodiment, the method involves administering a Pin1 protein or nucleic acid molecule as therapy to compensate for reduced or aberrant Pin1 expression or activity.

Stimulation of Pin1 activity is desirable in situations in which Pin1 is abnormally downregulated and/or in which increased Pin1 activity is likely to have a beneficial effect. For example, stimulation of Pin1 activity is desirable in situations in which a Pin1 is downregulated and/or in which increased Pin1 activity is likely to have a beneficial effect.

The present invention further includes therapeutic methods which utilize a combination of therapeutic agents of the invention, as described herein, and further therapeutic agents which are known in the art. Specifically, a Pin1 modulator of the present invention can be used in combination with a second modulator or with a second "abnormal cell growth inhibitory agent" (ACI agent). The ACI agent can be any therapeutic agent which can be used to treat the selected Pin1-associated disorder and/or cancer. One skilled in the art would be able to select appropriate ACI agents for combination therapy with a Pin1 modulator. For example, an ACI agent may be a second Pin1 modulator, or it may be an art-recognized agent which does not modulate Pin1.

The terms "abnormal cell growth inhibitory agent" and "ACI agent" are used interchangeably herein and are intended to include agents that inhibit the growth of proliferating cells or tissue wherein the growth of such cells or tissues is undesirable. For example, the inhibition can be of the growth of malignant cells such as in neoplasms or benign cells such as in tissues where the growth is inappropriate. Examples of the types of agents which can be used include chemotherapeutic agents, radiation therapy treatments and associated radioactive compounds and methods, and immunotoxins.

The language "chemotherapeutic agent" is intended to include chemical reagents which inhibit the growth of proliferating cells or tissues wherein the growth of such cells or tissues is undesirable. Chemotherapeutic agents are well known in the art (see e.g., Gilman A. G., et al., *The Pharmacological Basis of Therapeutics,* 8th Ed., Sec 12:1202-1263 (1990)), and are typically used to treat neoplastic diseases, tumors, and cancers.

The language "radiation therapy" is intended to include the application of a genetically and somatically safe level of x-rays, both localized and non-localized, to a subject to inhibit, reduce, or prevent symptoms or conditions associated with undesirable cell growth. The term x-rays is intended to include clinically acceptable radioactive elements and isotopes thereof, as well as the radioactive emissions therefrom. Examples of the types of emissions include alpha rays, beta rays including hard betas, high energy electrons, and gamma rays. Radiation therapy is well known in the art (see e.g., Fishbach, F., *Laboratory Diagnostic Tests,* 3rd Ed., Ch. 10: 581-644 (1988)), and is typically used to treat neoplastic diseases, tumors, and cancers.

The term "immunotoxins" includes immunotherapeutic agents which employ cytotoxic T cells and/or antibodies, e.g., monoclonal, polyclonal, phage antibodies, or fragments thereof, which are utilized in the selective destruction of undesirable rapidly proliferating cells. For example, immunotoxins can include antibody-toxin conjugates (e.g., Abricin and Ab-diptheria toxin), antibody-radiolabels (e.g., Ab-$I^{135}$) and antibody activation of the complement at the tumor cell. The use of immunotoxins to inhibit, reduce, or prevent symptoms or conditions associated with neoplastic diseases are well known in the art (see e.g., Harlow, E. and Lane, D., *Antibodies,* (1988)).

The language "inhibiting undesirable cell growth" is intended to include the inhibition of undesirable or inappropriate cell growth. The inhibition is intended to include inhibition of proliferation including rapid proliferation. For example, the cell growth can result in benign masses or the inhibition of cell growth resulting in malignant tumors. Examples of benign conditions which result from inappropriate cell growth or angiogenesis are diabetic retinopathy, retrolental fibrioplasia, neovascular glaucoma, psoriasis, angiofibromas, rheumatoid arthritis, hemangiomas, Karposi's sarcoma, and other conditions or dysfunctions characterized by dysregulated endothelial cell division.

3. Pharmacogenomics

The Pin1 molecules of the present invention, as well as agents, or modulators which have a stimulatory or inhibitory effect on Pin1 activity (e.g., Pin1 gene expression) as identified by a screening assay described herein can be administered to individuals to treat (prophylactically or therapeutically) disorders (e.g, proliferative disorders such as cancer) associated with aberrant Pin1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a Pin1 molecule or Pin1 modulator as well as tailoring the dosage and/or therapeutic regimen of treatment with a Pin1 molecule or Pin1 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict a drug response. According to this method, if a gene that encodes a drug target is known (e.g., a Pin1 protein or Pin1 receptor of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a Pin1 molecule or Pin1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual will receive. This knowledge, when applied to dosing or drug selection, can avoid adverse reactions or therapeutic failure and thus enhance therapeutic or prophylactic efficiency when treating a subject with a Pin1 molecule or Pin1 modulator, such as a modulator identified by one of the exemplary screening assays described herein.

4. Use of Pin1 Molecules as Surrogate Markers

The Pin1 molecules of the invention are also useful as markers of disorders or disease states, as markers for precursors of disease states, as markers for predisposition of disease states, as markers of drug activity, or as markers of the pharmacogenomic profile of a subject. Using the methods described herein absence and/or quantity of the Pin1 molecules of the invention may be detected, and may be correlated with one or more biological states in vivo. For example, the Pin1 molecules of the invention may serve as surrogate markers for one or more disorders or disease states or for conditions leading up to disease states.

As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the causation of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258-264; and James (1994) *AIDS Treatment News Archive* 209.

The Pin1 marker molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a Pin1 marker) transcription or expression, the amplified marker may be in a quantity which is more readily detectable than the drug itself. Also, the marker may be more easily detected due to the nature of the marker itself; for example, using the methods described herein, anti-Pin1 antibodies may be employed in an immune-based detection system for a Pin1 protein marker, or Pin1-specific radiolabeled probes may be used to detect a Pin1 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90:229-238; Schentag (1999) *Am. J. Health-Syst. Pharm.* 56 Suppl. 3:S21-S24; and Nicolau (1999) *Am. J. Health-Syst. Pharm.* 56 Suppl. 3:S16-S20.

The Pin1 marker molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12):1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., Pin1 protein or RNA) for specific tumor markers in a subject, a drug or course of treatment may be selected that is optimized for the treatment of the specific tumor likely to be present in the subject. Similarly, the presence or absence of a specific sequence mutation in Pin1 DNA may correlate Pin1 drug response. The use of pharmacogenomic markers therefore permits the application of the most appropriate treatment for each subject without having to administer the therapy.

This invention is further illustrated by the following examples which should not be construed as limiting. The following examples show the use of Pin1 as a universal marker for abnormal cell growth, e.g., cancer and the involvement of Pin1 in tumorigenic pathways. The contents of all references, patents and published patent applications cited throughout this application, as well as the Figures, are incorporated herein by reference.

EXAMPLES

Example 1

Tissues with Elevated Pin1 Levels

Automated cellular imaging system (ACIS) was used to determine tissues with elevated Pin1 Levels. The data that is presented in Example 1 is from U.S. patent application Ser. No. 10/071,747, filed Feb. 8, 2002, the entire contents of which are incorporated by reference.

Micro-histoarray sections were scanned and images were captured using the automated cellular imaging system (ChromaVision Medical Systems, Inc., San Juan Capistrano, Calif.) which combines automated microscopy and computerized image processing to analyze of multiple tissues on a single slide. ACIS was used to analyze microarray tissue sections on glass slides stained using a diaminodenzidine chromagen (DAB) and hematoxylin counterstain. Positive staining (brown color) as viewed by light microscope indicates the presence of the protein, and color intensity correlates directly with protein quantity (expression). The ACIS was able to recognize 255 levels of immnohistochemical staining intensity (0-255) and converted these to fractional scores for the selected individual areas. However, the base limit on the threshold for the Generic DAB is pre-set at 50 by the manufacturer because the system is very sensitive. Therefore, any intensity below 50 was treated. as 0 in this study. Entire immunostained tissue sections were scanned using the 4× objective and images were captured using the 10× objective.

Calculation of Pin Protein Expression in Human Cancers

In this study, intensity scoring and the percent positive scoring (brown area was divided by total area) were used with the entire individual tissue dot selected. The immunohistochemical staining was quantitated without knowledge of a pathologist's score. All tissue samples were immunostained twice in University of Basel and in Pintex Pharmaceuticals, Inc. and the two data sets were evaluated in Pintex Pharmaceuticals, Inc. The final score was obtained by using the average of two data sets and calculated by the formulation:

score=intensity+(X percent positive staining).

The % of total cases showing elevated levels (over-expression) of Pin 1=[numbers of tumor samples with score larger than the score of the highest normal case)
total number of tumor samples Results

TABLE 1

Pin1 protein over-expression in human tissues microarray

| Tumor type | Case number | % of Tumor Cases with Eleveted Level of Pin1 |
|---|---|---|
| Brain tumor (3) | 111 | |
| Oligodendroglioma | 20 | 90 |
| Astrocytoma | 46 | 63 |
| Glioblastomamultiforme | 45 | 87 |
| Genecological tumor (13) | 372 | |
| Cervical carcinoma | 42 | 81 |
| Endometrium, endometroid carcinoma | 46 | 0 |
| Endometrium, serous carcinoma | 13 | 0 |
| Ovary, endometroid cancer | 45 | 24 |
| Ovary, Brenner tumor | 8 | 63 |
| Ovary mucinous cancer | 12 | 58 |
| Ovary, serous cancer | 47 | 43 |
| Uterus, carcinosarcoma | 6 | 100 |
| Breast, lobular cancer | 36 | 56 |
| Breast, ductal cancer | 47 | 47 |
| Breast, medullary cancer | 24 | 29 |
| Breast, mucinous cancer | 24 | 29 |
| Breast tubular cancer | 22 | 9 |
| Endocrine tumor (8) | 213 | |
| Thyroid adenocarcinoma | 42 | 29 |
| Thyroid follicular cancer | 49 | 41 |
| Thyroid medullary cancer | 8 | 100 |
| Thyroid papillary car | 36 | 22 |
| Parathyroid, adenocarcinoma | 28 | 21 |
| Adrenal gland adenoma | 15 | 0 |
| Adrenal gland cancer | 6 | 33 |
| Pheochromocytoma | 29 | 0 |
| Digestive tract tumor (11) | 411 | |
| Colon adenoma mild displasia | 47 | 21 |
| Colon adenoma moderate displasia | 47 | 17 |
| Colon adenoma severe displasia | 49 | 14 |
| Colon adenocarcinoma | 43 | 2 |
| Esophagus adenocarcinoma | 43 | 30 |
| Hepatocelluar carcinoma | 34 | 62 |
| Mouth cancer | 46 | 93 |
| Gall bladder adenocarcinoma | 28 | 14 |
| Pancreatic adenocarcinoma | 43 | 2 |
| Small intestine adenocarcinoma | 10 | 0 |
| Stomach diffuse adenocarcinoma | 21 | 0 |
| Genitourinary tract tumor (9) | 381 | |
| Prostate (hormone-refract) | 44 | 59 |
| Prostate (untreated) | 47 | 64 |
| Kidney chromophobic carcinoma | 15 | 0 |
| Kidney clear cell carcinoma | 47 | 0 |
| Kidney oncocytoma | 8 | 0 |
| Kidney papillary carcinoma | 44 | 0 |
| Testis, non-seminomatous cancer | 43 | 2 |
| Testis seminoma | 47 | 2 |
| Urinary bladder transitional carcinoma | 86 | 2 |
| Respiratory tract tumor (4) | 184 | |
| Lung, adenocarcinoma | 44 | 27 |
| Lung, large cell cancer | 45 | 42 |
| Lung, small cell cancer | 47 | 57 |
| Lung, squmous cell carcinoma | 48 | 44 |
| Hematological neoplasia (5) | 146 | |
| Hodgkin lymphoma | 23 | 0 |
| MALT lymphoma | 47 | 4 |
| NHL, diffuse large B | 22 | 18 |
| NHL, others | 30 | 23 |
| Thymoma | 24 | 8 |
| Skin tumor (5) | 178 | |
| Skin, malignant melanoma | 44 | 73 |
| Skin, basolioma | 44 | 39 |
| Skin, squamous cell cancer | 39 | 13 |
| Skin, merkel zell cancer | 5 | 100 |
| Skin benign nevus | 46 | 52 |
| Soft tissue tumor (2) | 45 | |
| Lipoma | 25 | 20 |
| Liposarcoma | 20 | 75 |

Example 2

Determination of Pin1 Levels in Normal Tissues

This example provide a method for evaluating the level of Pin1 in a tissue sample. Using this method the level of Pin1 in normal human tissue samples was determined. Based on these results, the tissue are grouped into three categories based on the level of Pin1.

Cell Lines. 12 human cell lines (WI 38, MCF10a, RPMI 7951, SW620, SW1271, DU145, PC-3, T98G, DBTRG-05MG, MDA-MB-435, MCF7) were obtained from the American Type Culture Collection (Manassas, Va.) and T47D was obtained from Arizona cancer center. Cells were cultured according to the instructions provided by the agency and provider.

Immunocytochemistry. Immunocytochemitry on cultured cells was performed as described previously (19), with following modifications. Cells were cultured on cover slides and fixed with 3% formaldehyde for 5 minutes at room temperature. Cells were permeabilized with 0.4% Triton X-100, followed by immersed in 3% H2O2/methanol for 15 minutes to block endogenous peroxidase. Cells then were incubated with anti-Pin1 polyclonal antibodies overnight at 4° C. and then biotinylated secondary goat anti-rabbit IgG antibodies (Vector Laboratories). Immunoreactivity was detected using a Vectastain Elite ABC kit (Vector Laboratories, Burlingame, Calif.) according to the manufacturer's instructions.

Immunoblotting Analysis. To detect Pin1 levels using immunoblotting analysis, cell lysates were obtained by sonication of cell pellets in 50 mM Tris-HCl pH 8.0, 150 mM NaCl, 0.5% Triton X-100, 10 µg/ml PMSF, and 20 µg/ml leupeptin, as described (15). Lysates were clarified by centrifugation 14000×g for 2 minutes. Proteins were resolved by 15% SDS-PAGE (BioWhittaker; Rockland, Me.), then were transferred at 4° C. in 1×Tris-Glycine-SDS (Biorad; Hercules, Calif.) containing 20% methanol onto nitrocellulose. Immunoblotting was performed with anti-Pin 1 or anti-actin antibodies, as described (Wulf, et al. (2001) EMBO J. 20: 3459-3472). Bound antibodies were detected by ECL (Amersham-Pharmacia; Piscataway, N.J.). Levels of Pin1 and actin were quantified by densitometry using Imagequant software (Amersham-Pharmacia; Piscataway, N.J.), followed by expressing Pin1 levels as Pin1/actin ratios, as described (Wulf, et al. (2001) EMBO J. 20: 3459-3472). Ratios given are an average from three gels.

Human Tissue Sources. We used two different human tissue sources, conventional tissue sections and tissue microarrays. Large conventional sections of formalin-fixed, paraffin-embedded human tumor tissue were provided by The Cooperative Human Tissue Network (CHTN), which included 18 bladder cancer, 10 breast cancer, 19 colon cancer, 18 lung cancer, 30 ovary cancer and 3 prostate cancer samples. The tissue microarrays were provided by the Institute of Pathology, University of Basel (Switzerland). The normal tissue arrays included 609 samples from 50 different organs, whereas the multi-tumor arrays included 2041 patients' tumor samples representing 60 different tumor types. All tissue samples were formalin-fixed and paraffin-embedded. Each tissue dot in the microarrays had a diameter of 0.6 mm.

Immunohistochemistry on Human Tissues. To ensure the specificity of Pin1 immunostaining, Pin1 polyclonal antibodies were affinity-purified and the specificity of the antibody was tested by Western blotting. Furthermore, preabsorbed antibody by GST-Pin1 protein did not reveal any specific reactivity. To perform the immunohistochemistry, the sections were deparaffinized in xylene twice, ten minutes each; and rehydrated in graded ethanols (100, 95 and 75%), five minutes each; followed by immersed in 3% H2O2/methanol for 15 minutes to block endogenous peroxidase. For antigen retrieval, the sections were microwaved in citrate buffer (pH 6.0) (BioGenex) gently boiling for 15 minutes. The sections were then blocked in 10% normal goat serum in TBS, followed by incubation with polyclonal Pin1 antibodies (0.4 µg/ml) overnight at 4° C. in a humidity container. Then the sections were incubated with biotinylated goat anti-rabbit IgG (Vector Laboratories, Vectastain Elite ABC Kit) diluted at 1:300 in 5% normal goat serum for 30 minutes at room temperature. The standard ABC process was then followed, according to the instructions. DAB was used as a chromogen, followed by counterstaining with hematoxylin.

Analysis and Quantification of Pin1 Immunostaining. After immunostaining, slides were evaluated by two different methods. Large regular sections of human tumor tissues obtained from CHTN were manually evaluated under the microscope, whereas tissue microarrays were evaluated manually under the microscope and automatically using Automated Cellular hnaging System (ACIS) (ChromaVision Medical Systems, Inc., San Juan Capistrano, Calif.). For ACIS, entire immunostained tissue sections were scanned using the 4× objective and then images were captured using the 10× objective by ACIS. ACIS combines automated microscopy and computerized image processing to analyze multiple tissues on a single slide. In this study, ACIS was used to analyze microarray tissue sections on glass slides stained using a diaminodenzidine chromagen (DAB), with hematoxylin counterstain. Positive staining (brown) as viewed by a light microscope indicates the presence of the protein, and the intensity of the color correlated directly with the amount of the protein. The ACIS was able to quantify immunohistochemical staining intensity for the selected individual areas. However, the base limit on the threshold for the generic DAB is pre-set at 50 by the manufacturer due to the high sensitivity of the system. Therefore, any intensity below 50 was treated as 0 in this study, as suggested by the manufacturer.

Results

Higher Pin1 levels were previously found in human breast carcinoma-derived cell lines in comparison with normal human mammary epithelial cell lines or a spontaneously immortalized normal human mammary epithelial cell line. To determine Pin1 expression in other tumor cell lines, Pin1 levels in five human cell lines was determined by immunocytochemistry: a normal fibroblast cell line (WI38), a melanoma cell line (RPMI7951), a colon cancer cell line (SW620), two prostate cancer cell lines (PC3 and DU145). When immunostained with Pin1 antibodies, all cell lines had Pin1 staining predominantly in the nucleus, which is consistent with previous findings that Pin1 is primarily located in the nucleus of cultured cells. However, the levels of Pin1 protein varied between cell types with normal fibroblast cells showing the lowest Pin1 level and the PC3 cell line showing highest Pin1 level.

To confirm these immunostaining results, human tumor cell lines from multiple tumor types were screened for Pin1 levels by Western blotting. The results were semi-quantitatively evaluated and internally controlled by actin, with the final results shown as a Pin1/actin ratio for each cell line examined (Table 2). Pin1 protein levels were determined for twelve human cell lines: a normal fibroblast cell line (WI-38), a spontaneously immortalized normal mammary epithelial cell line (MCF-10A), breast tumor cell lines (MDA-MB-435, T47D, MCF-7), glioblastoma cell lines (T98G, DBTRG-05MG), prostate tumor cell lines (PC-3, DU 145), a colon tumor cell line (SW620), a small cell lung cancer cell line (SW1271) and a melanoma cell line (RPMI7951). All cell lines examined had detectable Pin1 protein. The lowest levels of Pin1 consistently obtained from the "normal" cell lines, WI-38 (fibroblasts) and MCF-10A (a spontaneously immortalized normal human mammary epithelial cell line). All tumor cell lines contained higher levels of Pin1 than the "normal" cell lines with two of the tumor cell lines, SW620 (colon cancer) and PC-3 (prostate cancer) consistently containing the highest levels of Pin1. These results have not only confirmed but also expanded previous findings that Pin1 levels are higher in tumor cell lines than those in normal cell.

TABLE 2

The average Pin 1/actin level from three western blots.

| Lane in FIG. 2 | Cell Line | Cell Type | Pin1/Actin |
|---|---|---|---|
| 1 | SW 1271 | Lung (Small Cell) | 1.6 ± 0.3 |
| 2 | DBTRG 05MG | Glioma | 1.8 ± 0.1 |
| 3 | T98G | Glioma | 2.1 ± 0.5 |
| 4 | MDAMB 435 | Breast | 2.1 ± 0.3 |
| 5 | MCF 10A | Breast | 1.2 ± 0.0 |
| 6 | MCF 7 | Breast | 1.9 ± 0.1 |
| 7 | T47D | Breast | 2.4 ± 0.3 |
| 8 | DU 145 | Prostate | 1.9 ± 0.2 |
| 9 | PC 3 | Prostate | 3.2 ± 0.4 |
| 10 | SW 620 | Colon | 3.0 ± 0.4 |
| 11 | RPMI 7951 | Melanoma | 1.9 ± 0.2 |
| 12 | WI 38 | Fibroblast | 1.0 ± 0.0 |

MCF-10A and WI-38 are cell lines derived from human normal tissues. SW1271, DBTRG-05MG, T98G, MDA-MB-435, MCF 7, T47D, DU 145, PC-3, SW 620, and RPMI 7951 are cell lines derived from human tumor tissues.

Pin1 Levels in Human Normal Tissues.

Before examining the Pin1 levels in human cancer tissues, the levels were examined in a large number (609 tissue samples) of the normal tissues provided by the Institute of Pathology, University of Basel (Switzerland). Normal tissue contains multiple cell types since cancers are typically derived from one particular cell type of normal tissues, all samples were examined in detail and Pin1 levels were evaluated by each individual cell type. Pin1 levels were undetectable or very low (with the score of 0 to 1+) in 49 cell types present in most normal human tissues examined (Table 3). Moderate to medium Pin1 positive staining (with the score of 2+) was observed in 29 cell types (Table 4). High Pin1 level (with the score of 3+) was observed in only four cell types, which were: ciliated cells in fallopian tube, lung bronchi and nose paranasal sinus; granulose cell layer in ovary; cytotrophoblast, endothelial cells in fetal capillaries and mesenchymal cells found in placenta (Table 5). These results indicate that Pin1 is normally expressed at very low levels in most normal tissues, although significant levels of Pin1 are generally found in cell types that normally undergo active cell division.

Study on Conventional Human Tissue Sections. As an initial step to evaluate Pin1 expression in different human cancer tissues, 98 large conventional tissue sections of human tumor samples were obtained from The Cooperative Human Tissue Network (CHTN), which included 18 bladder cancer, 10 breast cancer, 19 colon cancer, 18 lung cancer, 30 ovary cancer and 3 prostate cancer samples. When immunostained with anti-Pin1 antibodies and evaluated under the microscope, Pin1 positive staining was readily identified in both the nucleus and cytoplasm in 10 of 18 bladder, 10 of 10 breast, 9 of 19 colon, 12 of 18 lung, 2 of 3 prostate and 5 of 30 ovary cancer samples. Although these results were not directly compared with the corresponding normal tissues, they suggested that Pin1 may be overexpressed in many different tumors at rather high incidences.

Large-scale Quantitative Study on Human Tissue Microarrays. To confirm the above initial observation that Pin1 is overexpressed in many different human cancers, a large-scale study using human tissue microarrays was preformed to examine Pin1 protein levels in many different human cancer tissues as well as the corresponding normal tissues. Microarray technology is currently a critical new technology that allows for rapid analysis of several hundred tumor samples in expedited experimental approaches. This relatively new tumor tissue technology had recently shown potential in rapidly identifying and characterizing genes and markers involved in the pathogenesis of human cancers (20-22). The human tissue microarrays included 2041 tumor samples from 60 different tumor types and 609 normal samples from 50 different organ and/or tissues/cell types.

After immunostaining with Pin1 antibodies, Pin1 levels were independently scored manually by a pathologist (G. S.) using a conventional microscope or automatically by Automated Cellular Imaging System (ACIS). For manual evaluation, all immunostained samples were evaluated in one day to maximize the internal consistency. The staining intensity was scored in a four-step scale (0, 1, 2, 3). For the automatic analysis, on each sample we first selected three small circles that contain tumors and then measured the average of the Pin1 intensity and percentage of Pin1 positive tumor cells (selected brown area was divided by total selected area). The final Pin1 score was calculated based on the formulation (Pin1 Score=intensity+percent positive staining). This score was arbitrarily designed based on our observations that after subtracting the background of 50, the maximal intensity was about 100, which was similar to maximal percentage of Pin1 positive cells. Therefore, two parameters are equally weighed.

To determine the correlation between manual and automated analyses, we analyzed the correlation between the scores obtained from manual and automatic evaluation procedures in selected tumors with various levels of Pin1 expression. When manual evaluation was compared with automated analysis, we found a significant correlation between these two methods. For example, in 104 brain tumors where Pin1 is highly overexpressed, the Pearson's coefficient of correlation was 0.84 (p<0.001) (FIG. 4B). Similar results were also obtained in kidney tumors (n=114; the Pearson's coefficient of correlation (r), 0.86; p<0.001), lung tumors (n=183; r=0.85; p<0.001), in breast tumors (n=149; r=0.67; p<0.001), prostate tumors (n=91; r=0.7; p<0.001) and ovary tumors (n=116; r=0.76; p<0.001) (data not shown). These results indicate that both manual and automatic procedures produce similar results in evaluating Pin1 expression in human tissues arrays.

Pin 1 Levels in Human Tumor Tissues. Given that the automatic evaluation procedure can be used to quantify Pin1 expression in a large number of samples and in a less subjective manner, we used this method to compare Pin1 staining in 2041 samples from total 60 different tumor types with the corresponding normal tissue. Of note, Pin1 levels in carcinoid and paraganglioma were found to be high, but were not shown because of the difficulty in finding corresponding normal tissues. From our quantitatively evaluated results, we have identified three major groups based upon the Pin1 score.

In the first group, we have identified 38 of 60 tumor types that had more than 10% of cases with elevated Pin1 levels relative to the corresponding normal tissue. Among these cancers, some of the common cancers demonstrated elevated Pin1 levels in high incidence, including prostate, cervical, brain, lung, breast, colon, liver cancer and melanoma. Interestingly, cancers such as small cell lung cancer and liposarcoma, which come from the same cell type origin, both demonstrated high Pin1 levels at high incidence. In the second group, we identified some types of tumors where Pin1 levels were similar those present in the corresponding normal tissues. These tumors included skin squamous cell cancer, gall bladder adenocarcinoma, esophagus adenocarcinoma, thyroid papillary carcinoma, breast tubular cancer, and colon adenocarcinoma. Finally, in third group Pin1 levels were lower than those present in the corresponding normal tissues. These tumors included kidney, testis, adrenal gland and stomach tumors (FIG. 7). These results indicate that Pin1 overexpression is a specific and prevalent event in human cancers.

Results

The results of the Pin1 experiments are represented in the following Tables. The data was grouped into three categories. Category one was tissue with low Pin1 levels, category 2 was tissue with moderate to high levels of Pin1 and Category 3 was tissues with high levels of Pin1 (see Tables 3, 4, and 5, respectively).

TABLE 3

Normal Human Tissue with Low Level of Pin1.

| Cell type | Sub-category | Organ | Pin1 intensity (+) |
|---|---|---|---|
| absorptive cell | mucosa | small intestine, duodenum, appendix, colon descendens, rectum | 1 |
| acidophilic cell | adenohypophysis | Pituitary gland, anterior lobe | 1 |
| astrocytes | cerebrum, grey matter, white matter | cerebrum | 1 |
| basal cell | Epidermis, Basal layer, urothelium, thin limb of Henle loop, epididymal tubule | Skin, surface; kidney pelvis, mucosa; urinary bladder, urothelium; kidney, medulla; epididymis | 1 |
| basophilic cell | adenohypophysis | Pituitary gland, anterior lobe | 1 |
| centroacinar cell | intercalated ducts | pancreas | 1 |
| chief cell | parenchyma | parathyroid gland | 1 |
| chromophobe cell | adenohypophysis | Pituitary gland, anterior lobe | 1 |
| clear cell | hair, outer rooth sheet | skin (hairs, sebaceous glands) | 1 |
| columnar ductal cell | duct, epithelium | parotid gland, submandibullary gland, sublingual gland, lip, small salivary gland, seminal vesicle | 1 |
| cytotrophoblast | villous parenchyma | placenta, tonsil (deep) | 1 |
| Dendritic reticulum cell | follicle | lymph node, tonsil, deep | 1 |
| endothelial cell | intramuscular vessel | urinary bladder, muscular wall, lip | 1 |
| fibroblast/cyte | Lobuloalveolar unit, endocervix, oral mucosa | breast glands, endocervix, lip | 1 |
| flat epithelial cell | thin limb of Henle loop | kidney, medulla | 1 |
| Follicle center blast/cyte | lamina propria | appendix | 1 |
| follicle center macrophage | follicle, lamina propria | lymph node, tonsil, deep, appendix | 1 |
| functional cell layer | mucosa | esophagus, mucosa | 1 |
| glial cell (pituicytes) | neurohypophysis | Pituitary gland, posterior lobe | 1 |
| granulosa-lutein cell | corpus luteum | ovary, corpus luteum | 1 |
| intercalated cell | collecting duct | kidney, medulla | 1 |
| intermediate cell | urothelium | kidney pelvis, mucosa | 1 |
| intermediate cell | urothelium, thin limb of Henle loop | urinary bladder, urothelium, kidney (medulla) | 1 |
| intraep lymphocytes | mucosa | rectum | 1 |
| Keratinocytes, bottom | Epidermis, squamous layer | Skin surface, anal canal, skin | 1 |

TABLE 3-continued

Normal Human Tissue with Low Level of Pin1.

| Cell type | Sub-category | Organ | Pin1 intensity (+) |
|---|---|---|---|
| luminal A cell and B cell | lobuloalveolar unit | breast, glands | 1 |
| lymphocyte | muscularis propria, exocervix, lamina propria, submucosa | stomach muscular wall, exocervix, kidney pelvis mucosa, urinary bladder, urothelium, stomach antrum, stomach fundus and corpus, small intestine duodenum, ileum, colon descendens, gallbladder, lung bronchial glands, nose paranasal sinus, endocervix, | 1 |
| lymphoid cell, -blast, -cyte | follicle | lymph node, tonsil deep | 1 |
| mesenchymal cell | villous parenchyma | placenta, mature | 1 |
| midzone cell-layer | exocervix | exocervix | 1 |
| myocyte | muscularis propria | stomach, muscular wall | 1 |
| nerve fibres | cerebrum, grey matter, white matter | cerebrum | 1 |
| parietal epithelial cell | glomerulus | kidney, cortex | 1 |
| perifollicular lymphocyte | lamina propria | appendix | 1 |
| pneumocyte type 1* (squamous) | acinus | lung, parenchyma | 1 |
| prickle cell layer* | mucosa | esophagus, mucosa | 1 |
| principal cell | collecting duct | kidney, medulla | 1 |
| Schwann cell | nerve plexus, nerves | stomach muscular wall, penis (glans, corpus spongiosum) | 1 |
| sebaceous gland cell | hairs, sebaceous glands | skin (hairs, sebaceous glands) | 1 |
| serous cell | acinus | sublingual gland | 1 |
| smooth muscle cell | muscularis propria | appendix muscular wall, ileum, muscular wall, urinary bladder muscular wall | 1 |
| spermatid | seminiferous tubules | testis | 1 |
| spermatogonium | seminiferous tubules | testis | 1 |
| squamous cell | oral mucosa | oral cavity | 1 |
| superficial cell | urothelium, thin limb of Henle loop | kidney pelvis mucosa, urinary bladder urothelium, kidney medulla | 1 |
| tall columnar cell (=principle cell) | epididymal tubule | epididymis | 1 |
| theca externa cell | follicle cyst | ovary, follicular cyst | 1 |
| thyrocyte | follicle | thyroid | 1 |
| visceral epithelial cell (=podocytes) | glomerulus | kidney, cortex | 1 |

TABLE 4

Normal Human Tissue with Moderate to High Level of Pin1

| Cell Type | Subsub-category | Organ | Pin1 intensity (+) |
|---|---|---|---|
| basal cell | tonsil surface epithelium, Epidermis Basal layer, prostatic glands | tonsil surface, anal canal, skin, prostate | 2 |

TABLE 4-continued

Normal Human Tissue with Moderate to High Level of Pin1

| Cell Type | Subsub-category | Organ | Pin1 intensity (+) |
|---|---|---|---|
| chief cell | mucosa | stomach, fundus and corpus | 2 |
| columnar cell (surface epithelium) | mucosa | gallbladder | 2 |
| columnar secretory cell | prostatic glands | prostate | 2 |
| connecting tubule cell | connecting tubule | kidney, cortex | 2 |
| cortical cell | cortex | adrenal gland | 2 |
| decidual cell | maternal decidual tissue | placenta, early, decidua | 2 |
| endometrial stromal cell | endometrium, proliferation, early secretion | endometrium, proliferation and secretion | 2 |
| endothelial cell | blood vessel, intramuscular vessel, vessels, glomerulus | ileum muscular wall, colon descendens muscular wall, kidney pelvis muscular wall, penis glans and corpus spongiosum, Skin surface, oral cavity, urinary bladder, urothelium, kidney cortex | 2 |
| fibroblast | intima | aorta intima, | 2 |
| glandular cell | endometrium, proliferation, early secretion | endometrium proliferation secretion, | 2 |
| intraep lymphocytes | tonsil, lymphocytes, | tonsil, surface | 2 |
| intraep lymphocytes | Epidermis | anal canal, skin | 2 |
| islet cell (β-cell (insulin), alpha-cell (glucagon), ∂-cell (somatostatin), PP-cell (pancreatic polypeptide) | islet sells | pancreas | 2 |
| lymphocyte | muscularis propria, dermis, oral mucosa, | esophagus muscular wall, kidney pelvis muscular wall, oral cavity | 2 |
| mucous-secreting cell | mucosa | stomach, antrum | 2 |
| neuron | Outer molecular layer | cerebellum, cortex | 2 |
| parietal cell | mucosa | stomach, fundus and corpus | 2 |
| pheochromocyte | medulla | adrenal gland | 2 |
| primary spermatocyte | seminiferous tubules | testis | 2 |
| Schwann cell | nerve plexus, nerves | appendix muscular wall, esophagus muscular wall, ileum muscular wall, ileum muscular wall, kidney pelvis muscular wall | 2 |
| secondary spermatocyte | seminiferous tubules | testis | 2 |
| serous cell | submucosa | lung, bronchial glands | 2 |
| squamous cell | tonsil, surface epithelium | tonsil, surface | 2 |
| suprabasal cell | mucosa, anal transition zone | anal canal, transition epithelium | 2 |
| tall slender cell (=apical cell) | epididymal tubule | epididymis | 2 |
| theca interna cell (=theca-lutein cell | follicle cyst | ovary, follicular cyst | 2 |
| thymocyte (small lymphocyte) | cortex and medulla | thymus | 2 |
| tubular cell | proximal tubule and distal tubule | kidney, cortex | 2 |

TABLE 5

Normal Human Tissue with High Level of Pin1

| Cell Type | Sub-category | Organ | Pin1 intensity (+) |
|---|---|---|---|
| ciliated cell | mucosa, nonstratified epithelium | lung bronchi, nose paranasal sinus, fallopian tube | 3 |
| granulosa cell layer | follicle cyst | ovary, follicular cyst | 3 |
| Cytotrophoblast | villous parenchyma | placenta, first trimenon | 3 |
| mesenchymal cell | villous parenchyma | placenta, first trimenon | 3 |
| endothelial cell fetal capillaries | villous parenchyma | placenta, first trimenon | 3 |

Out of 84 cell types in 50 different normal organs in the human body examined, Pin1 was generally expressed at very low levels in most normal tissues and its expression was typically associated with cell proliferation, with high Pin1 level being found only in a few cell types. Pin1 was strikingly overexpressed in many different human cancers. Out of 60 human cancer types, Pin1 overexpression was found in 38 types that showed more than 10% of cases with elevated Pin1 levels relative to the corresponding normal tissue including most common human cancers such as prostate, cervical, brain, lung, breast, colon, liver cancer and melanoma. These results indicate that Pin1 overexpression is prevalent and specific in human cancers. Given that inhibition of Pin1 can suppress transformed phenotypes and inhibit tumor cell growth, and that Pin1 expression is an excellent prognostic marker in prostate cancer, these findings have important implications for the pathogenesis, diagnosis and treatment of human cancers.

Pin1 has been shown to play a critical role in the cell cycle (Lu, et al. (2002) Trends Cell Biol. 12: 164-172). Consistent with this idea, Pin1 expression is generally associated with cell proliferation in the normal human body. Undetectable or low levels of Pin1 are detected in most differentiated cell types such as smooth muscle cell, astrocytes, fibroblast, glial cell and nerve fibers. Significant levels of Pin1 are found in some cell types that normally undergo active cell division such as primary and secondary spermatocytes, but in spermatid in testis. Interestingly, there are a few exceptions. For example, Pin1 is not present in glial cells, but is present in neurons at rather high concentrations. This is consistent with the previous findings that Pin1 plays an important role in neuronal function (Zhou, et al. (2000) Mol Cell. 6: 873-883; Lu, et al. (1999) Nature. 399: 784-788). It is interesting to note that high levels of Pin1 are observed in ciliated cells found in fallopian tube, lung bronchi and nose paranasal sinus, granulose cell layer in ovary and cytotrophoblast, endothelial cells in fetal capillaries and mesenchymal cells in placenta, although their biological significance remains to be determined.

Given that Pin1 specifically isomerizes many critical phosphorylated Ser/Thr-Pro motifs, the most common phosphorylation sites in oncogenic pathways (Blume-Jensen, et al (2001) Nature. 411: 355-365; Hanahan, et al. (2000) Cell. 100: 57-70), it is conceivable that Pin1 is an indispensable translator and amplifier of oncogenic signal transduction, which respond to and translate oncogenic signaling into cell proliferation and transformation.

Pin1 is normally expressed at very low levels in most normal tissues and Pin1 knockout mice do reach adulthood despite some cell proliferative abnormalities, especially in old age (Liou, et al. (2002) Proc. Natl. Acad. Sci. USA. 99: 1335-1340; Fujimori, et al. (1999) Biochem Biophys Res Commun. 265: 658-663), it is reasonable to assume that a specific anti-Pin1 therapy might not have general toxic effects. However, the feasibility of therapeutic Pin1 inhibition has not yet been explored due to the lack of Pin1 specific inhibitors. Therefore, there is a need for the development of Pin1 specific inhibitors. Such Pin1-specific inhibitors may themselves be effective anti-cancer drugs or become valuable adjuncts to established chemo-therapeutic procedures.

In summary, by analyzing Pin1 expression in an usually large number of both normal and cancerous human tissues, it was found that Pin1 expression is normally associated with cell proliferation. Pin1 is expressed at relatively low levels in the vast majority of human normal tissues with a few exceptions. More importantly, Pin1 is highly overexpressed at a rather high frequency in many different tumors, including most common human cancers such as prostate, lung, colon, breast, brain tumors and melanoma. Together with the previous findings that Pin1 plays a pivotal role in breast cancer, these results suggest that Pin1 may play a critical role in the pathogenesis, diagnosis and treatment of many human cancers.

Example 3

Tissues with Pin1 Levels Less than in the Corresponding Normal Tissue

Using the data obtained in Examples 1 and 2, the tissues identified in Table 6 were identified as having lower Pin1 levels in cancerous tissue than in the corresponding normal tissue.

TABLE 6

Tissues with Decreased Pin1 Levels in Cancerous Tissue as Compared to Normal Tissue

| Tumor type | N | Score (int + %) |
|---|---|---|
| Endometrium, endometroid carcinoma | 46 | 0 |
| Endometrium, serous carcinoma | 13 | 0 |
| Adrenal gland adenoma | 15 | 0 |
| Pheochromocytoma | 29 | 0 |
| Pancreatic adenocarcinoma | 43 | 0 |
| Small intestine adenocarcinoma | 10 | 0 |
| Stomach diffuse adenocarcinoma | 21 | 0 |
| Kidney chromophobic carcinoma | 15 | 0 |
| Kidney oncocytoma | 8 | 0 |
| Kidney papillary carcinoma | 44 | 0 |
| Kidney clear cell carcinoma | 47 | 2 |
| Testis, non-seminomatous cancer | 43 | 2 |
| Testis seminoma | 47 | 0 |
| Hodgkin lymphoma | 23 | 0 |
| Skin, basolioma | 44 | 0 |

REFERENCES

Bailly et al. (1991) *Nature* 350:715-8
Blangy et al. (1995) *Cell* 83:1159-69
Bonnemann et al. (1996) *Curr Opinion Pediatr* 8:569-82. [a subsequent erratum appears in *Curr Opinion Pediatr* 1997 9:1961]
Bramblett et al. (1993) *Neuron* 10:1089-99
Clackson and Wells (1995) *Science* 267:383-6
Crenshaw et al. (1998) *EMBO J.* 17:1315-27
Davis et al. (1983) *Proc Natl Acad Sci USA* 80:2926-2930

Dolinski and Heitman (1997) Peptidyl-prolyl isomerases (PPIases). In: *Guidebook to Molecular Chaperones and Protein-Folding Catalysts, M.-J. eds. Gething, Oxford University Press*, pp.359-369
Dolinski et al. (1997) *Proc. Natl. Acad. Sci. USA* 94:13093-131098
Ermekova et al. (1998) *Adv Exp Med Biol* 446:161-80
Hanes et al. (1989) *Yeast* 5:55-72
Hani et al. (1995) *Febs Lett* 365:198-202
Heald and McKeon (1990) *Cell* 61:579-89
Huibregtse et al. (1995) *Proc Natl Acad Sci USA* 92:2563-7 [a subsequent erratum appears in *Proc Natl Acad Sci USA* 92:5249]
Hunter (1998) *Cell* 92:141-143
Izumi and Maller (1993) *Mol Biol Cell* 4:1337-50
King et al. (1994) *Cell* 79:563-571
Kops et al. (1998) *J. Biol. Chem.* 273:31971-6
Lu (1999) *Prog. Cell Cycle Res.* (1995;1 :187-205)
Lu et al. (1996) *Nature* 380:544-7
Lu and Hunter (1995a) *Cell* 81:413-424
Lu and Hunter (1995b) *Progress in Cell Cycle Research* 1:187-205
Lu et al. (1999) *Nature* 399: 784-788
Lu et al. (1998) *Science* 283:1325-1328
Macias et al. (1996) *Nature* 382:646-9
Maleszka et al. (1996) *Proc Natl Acad Sci USA* 93:447-51
Marchal et al (1998) *Mol Cell Biol* 18:314-321
Mayer and Baltimore (1993) *Trends Cell Biol* 3:8-13
Mayer et al. (1995) *Curr Biol* 5:296-305
Meyn (1997) *Oncology* 11:349-56 (see also discussion 356, 361 and 365)
Muschel et al. (1997) *Vitain Horm* 53:1-25
Nefsky and Beach (1996) *EMBO J.* 15:1301-12
Nigg (1995) *BioEssays* 17:471-480
Nurse (1994) *Cell* 79:547-550
Pawson and Schlessinger (1993) *Curr Biol* 3:434-442
Pawson and Scott (1997) *Science* 278:2075-80
Piccart and Di Leo (1997) *Semin Oncol* 24:S10-27-S10-33
Rahfeld et al. (1994) *FEBS Lett.* 343:65-69
Ranganathan et al. (1997) *Cell* 89:875-886
Rotin (1998) *Curr Top Microbiol Immunol* 228:115-33
Sabo et al. (1999) *J. Biol Chem* 274:7952-7
Schlessinger et aL (1995) *Nature* 373:536-9
Schreiber (1991) *Science* 251:283-7
Schutkowski et al. (1998) *Biochemistry* 3 7:5566-75
Shen et al. (1997) *Proc. Natl. Acad. Sci. USA* 94:13618-13623
Shen et al. (1998) *Genes Dev.* 12:706-720
Staub et al. (1996) *EMBO J.* 15:2371-80
Stukenberg et al. (1997) *Curr Biol* 7:338-48
Sudol, M. (1996) *Prog Biophys Mol Biol* 65:113-32
Uchida et al. (1999) *FEBS Lett.* 446:278-82
Winder (1997) *J Muscle Res Cell Motil* 18:617-29
Yaffe et al (1997) *Science* 278:1957-1960
Kuang et al. (1997) *Science* 278:1957-1960.
Yoshida and Ihara (1993) *J Neurochern* 61:1183-6
Young et al. (1994) *Protein Sci* 3:717-29
Zhou et al. (1995) *Nature* 373:536-9

EQUIVALENTS

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A method of detecting cancer in a mammal, comprising
assessing the level of Pin1 protein having the amino acid sequence set forth in SEQ ID NO: 2 in a test sample from the mammal, and
comparing the level of Pin1 protein in the test sample to the level of Pin1 protein in a control sample comprising corresponding normal cells,
wherein the level of Pin1 protein in the test sample and the control sample is assessed by contacting the test sample and the control sample with an antibody that binds to the amino acid sequence set forth in SEQ ID NO:2 under conditions suitable for binding of the antibody, and
wherein a lower level of Pin1 protein in the test sample compared to the level of Pin1 protein in the control sample is indicative that the mammal has cancer selected from the group consisting of endometroid carcinoma, endometrium serous carcinoma, adrenal gland adenoma, pheochromocytoma, pancreatic adenocarcinoma, small intestine adenocarcinoma, stomach diffuse adenocarcinoma, kidney chromophobic carcinoma, kidney oncocytoma, kidney papillary carcinoma, kidney clear cell carcinoma, testis non-seminomatous cancer, testis seminoma and Hodgkin's lymphoma.

2. The method of claim 1, wherein the test sample is a tissue sample.

3. The method of claim 1, wherein the antibody is a polyclonal antibody.

4. The method of claim 1, wherein the antibody is a monoclonal antibody.

5. The method of claim 1, wherein the antibody is detectably labeled.

6. The method of claim 5, wherein the detectable label is selected from the group consisting of a radioactive, enzymatic, biotinylated and fluorescent label.

7. The method of claim 2, wherein said tissue sample is selected from the group of tissue consisting of endometrium, adrenal gland, pancreas, intestine, stomach, kidney, and testis.

8. The method of claims 1, wherein said test sample is selected from the group consisting of endometrium, adrenal gland, pancreas, intestine, stomach, kidney, testis, and lymph.

9. The method of claim 1, wherein the mammal is a human.

10. The method of claim 5, wherein the level of Pin1 is determined by the intensity of the signal emitted by the labeled antibody bound to the test sample and to the control sample.

11. The method of claim 1, wherein the level of Pin1 is determined by the percentage of cells bound to the antibody in the test sample and control sample.

12. A method of determining whether a mammal has cancer selected from the group consisting of endometroid carcinoma, serous carcinoma, adrenal gland adenoma, pheochromocytoma, pancreatic adenocarcinoma, small intestine adenocarcinoma, stomach diffuse adenocarcinoma, kidney chromophobic carcinoma, kidney oncocytoma, kidney papillary carcinoma, kidney clear cell carcinoma, testis non-seminomatous cancer, testis seminoma and Hodgkin's lymphoma, the method comprising,
contacting a test sample with a Pin1 antibody that binds to the amino acid sequence set forth in SEQ ID NO:2 under conditions suitable for binding of the antibody, and
comparing the level of Pin1 antibody bound to a test sample to the level Pin1 antibody bound to a control sample comprising corresponding normal cells,
wherein a lower level of Pin1 antibody bound to the test sample compared to the level of Pin1 antibody bound to the control sample is indicative that the mammal has cancer.

13. The method of claim 12, wherein the level of Pin1 antibody is determined by the percentage of cells bound to the Pin1 antibody.

14. The method of claim 12, wherein the level of Pin1 antibody is determined by the intensity of the signal emitted by the labeled antibody.

* * * * *